(12) United States Patent
Olsen et al.

(10) Patent No.: US 8,575,096 B2
(45) Date of Patent: Nov. 5, 2013

(54) RAPID ACTING INSULIN ANALOGUES

(75) Inventors: Helle Birk Olsen, Allerød (DK);
Thomas Børglum Kjeldsen, Virum (DD); Per Balschmidt, Hørsholm (DK); Tine Glendorf, Lyngby (DK); Svend Havelund, Bagsværd (DK)

(73) Assignee: Novo Nordisk A/S, Bagsvaerk (DK)

( * ) Notice: Subject to any disclaimer, the term of this patent is extended or adjusted under 35 U.S.C. 154(b) by 387 days.

(21) Appl. No.: 12/673,226

(22) PCT Filed: Aug. 12, 2008

(86) PCT No.: PCT/EP2008/060596
§ 371 (c)(1),
(2), (4) Date: Mar. 30, 2010

(87) PCT Pub. No.: WO2009/021955
PCT Pub. Date: Feb. 19, 2009

(65) Prior Publication Data
US 2011/0021423 A1    Jan. 27, 2011

Related U.S. Application Data

(60) Provisional application No. 60/957,013, filed on Aug. 21, 2007.

(30) Foreign Application Priority Data

Aug. 13, 2007  (EP) ..................................... 07114215

(51) Int. Cl.
*C07K 14/62*    (2006.01)
(52) U.S. Cl.
USPC ............... 514/6.1; 514/6.3; 514/6.7; 514/6.9; 514/21.3; 530/303; 530/324
(58) Field of Classification Search
None
See application file for complete search history.

(56) References Cited

U.S. PATENT DOCUMENTS

| 5,716,927 A | * | 2/1998 | Balschmidt et al. | ........... 514/6.1 |
| 2011/0009314 A1 | * | 1/2011 | Naver et al. | .................... 514/6.1 |

FOREIGN PATENT DOCUMENTS

| EP | 0214826 | 3/1987 |
| WO | WO 03/094951 | 11/2003 |
| WO | WO 2006/053906 | 5/2006 |
| WO | WO2006053906 | * 5/2006 |
| WO | WO 2007/096332 | 8/2007 |

OTHER PUBLICATIONS

Kang et al Diabetes Care 1991.*
Kurtzhals et al. Diabetes 2000.*
Olsen et al. Biochemistry, 2000.*
Schwartz, G.P. et al., "A Highly Potent Insulin: Des-(B26-B30)-[$Asp^{B10}$, $Tyr^{B25}$-$NH_2$] insulin (human)" Proc. Natl. Acad. Sci. USA, 1989, vol. 86, pp. 458-461.
Heller, S.R., "Insulin Analogues", Current Medical Research and Opinion, 2002, vol. 18, Suppl 1, pp. S40-S47.

* cited by examiner

*Primary Examiner* — Cecilia J Tsang
*Assistant Examiner* — Li Lee
(74) *Attorney, Agent, or Firm* — Michael J. Brignati

(57) ABSTRACT

The invention is related to fast acting insulin analogues which can form soluble mix-tures (pre-mixed or self-mixed) with long acting insulin analogues. The fast action is achieved through monomerizing substitutions/deletions in the C-terminus of the B-chain of human insulin and the mixability with long acting insulin analogues is achieved through a substitution of the Zn-binding His in position B10 of human insulin with a Gln amino acid residue. In one embodiment the invention is related to fast acting insulin analogues in which at least one of the natural amino acid residues in position B22-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 optionally have been deleted.

11 Claims, 6 Drawing Sheets

RAPID ACTING INSULIN ANALOGUES

CROSS-REFERENCE TO RELATED APPLICATIONS

This application is a 35 U.S.C. §371 national stage application of International Patent Application PCT/EP2008/060596 (published as WO 2009/021955 A1), filed Aug. 12, 2008, which claimed priority of European Patent Application 07114215.2, filed Aug. 13, 2007; this application further claims priority under 35 U.S.C. §119 of U.S. Provisional Application 60/957,013, filed Aug. 21, 2007.

FIELD OF THE INVENTION

The present invention is related to fast acting insulin analogues and pharmaceutical compositions comprising the fast acting insulin analogues and pharmaceutical compositions comprising the fast acting insulin analogues in mixture with long action insulin analogues.

BACKGROUND OF THE INVENTION

Insulin is a polypeptide hormone secreted by β-cells of the pancreas and consists of two polypeptide chains, A and B, which are linked by two inter-chain disulphide bridges. Furthermore, the A-chain features one intra-chain disulphide bridge.

The hormone is synthesized as a single-chain precursor of proinsulin (preproinsulin) consisting of a prepeptide of 24 amino acid followed by proinsulin containing 86 amino acids in the configuration: prepeptide B-Arg Arg-C-Lys Arg-A, in which C is a connecting peptide of 31 amino acids. Arg-Arg and Lys-Arg are cleavage sites for cleavage of the connecting peptide from the A and B chains to form the two-chain insulin molecule. Insulin is essential in maintaining normal metabolic regulation.

The hormone is secreted as defined hexamers which dissociate by dilution firstly into dimers and secondly into monomers. The active hormone is the insulin monomer. Destabilization of the insulin hexamer and/or the insulin dimer results in fast acting insulins like B28 Asp human insulin which is disclosed in EP 214826.

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a fast acting insulin to cover the insulin requirement related to meals.

Because diabetic patients are treated with multiple daily injections including protracted insulin supplied with multiple injections of a fast acting insulin, a combination of fast and long acting insulin in one injection will potentially save many injections. WO 2003/094951 discloses mixtures of a fast acting insulin analogue insulin aspart (B28Asp human insulin) and insulin detemir (Lys$^{B29}$ (N$^\epsilon$-tetradecanoyl) desB30 human insulin). However, mixtures of fast acting and long acting insulin analogues may suffer of a limited mixability resulting in that the fast acting insulin becomes less fast acting and the long acting insulin becomes less long acting.

It is the object of the present invention to provide improved fast acting insulins which have improved properties over the known fast acting insulins with respect to mixability with soluble, long acting insulin analogues.

SUMMARY OF THE INVENTION

In a first aspect the present invention is related to fast acting insulin analogues which can form soluble mixtures (pre-mixed or self-mixed) with long acting insulin analogues. The fast action is achieved through monomerizing substitutions/deletions in the C-terminus of the B-chain of human insulin and the mixability with long acting insulin analogues is achieved through a substitution of the Zn-binding His in position B10 of human insulin with a Gln amino acid residue.

In one embodiment the invention is related to fast acting insulin analogues in which at least one of the natural amino acid residues in position B22-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 optionally have been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B25-B30 optionally have been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further one or more of the natural amino acid residues in position B25, B26 and B30 optionally have been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further the natural amino acid residue in position B26 and B30 have been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further the natural amino acid residue in position B25 and B30 have been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further the natural amino acid residue in position B25 has been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further the natural amino acid residue in position B26 has been deleted.

In a further embodiment the invention is related to fast acting insulin analogues in which at least one of the natural amino acid residues in position B25-B30 in the human B-chain has been substituted with another amino acid residue having the effect of promoting formation of the monomeric form of insulin, the His amino acid residue in position 10 in the B-chain is substituted with a Gln and wherein further the natural amino acid residue in position B30 has been deleted.

In one embodiment not more than three of the amino acid residues in position B22-B30 or B25-B30 have been substituted with another amino acid residue. The substitutions may be the same or different.

In a further embodiment 1-2 of the amino acid residues in position B22-B30 or B25-B30 have been substituted with another amino acid residue and in a still further embodiment only one of the amino acid residues in position B22-B30 has been substituted with another amino acid residue.

In one embodiment the amino acid in position B22 is substituted with another amino acid residue.

In a further embodiment the amino acid in position B23 is substituted with another amino acid residue.

In a further embodiment the amino acid in position B24 is substituted with another amino acid residue.

In a further embodiment the amino acid in position B25 is substituted with another amino acid residue.

In a further embodiment the amino acid in position B26 is substituted with another amino acid residue.

In a further embodiment the amino acid in position B27 is substituted with another amino acid residue.

In a further embodiment the amino acid in position B28 is substituted with another amino acid residue.

In a further embodiment the amino acid in position B29 is substituted with another amino acid residue.

In a further embodiment the amino acid in position B30 is substituted with another amino acid residue.

In a further embodiment the amino acids in position B22 and position B28 are substituted with another amino acid residue which may be the same or different.

In a further embodiment the amino acids in position B22 and position B27 are substituted with another amino acid residue which may be the same or different.

In a further embodiment the amino acids in position B25 and position B27 are substituted with another amino acid residue which may be the same or different.

In a further embodiment the amino acids in position B25 and position B28 are substituted with another amino acid residue which may be the same or different.

In a further embodiment the amino acids in position B26 and position B27 are substituted with another amino acid residue which may be the same or different.

In a further embodiment the amino acids in position B26 and position B28 are substituted with another amino acid residue which may be the same or different.

In each of the previous embodiments the natural amino acid residue may be replaced by a Glu or an Asp amino acid residue.

In addition to substituting one or more of the amino acid residues in positions B22-B30 or B25-B30, one or more of these amino acid residues may also be deleted. Thus the modification in the area of the B-chain may be a combination of one or more substitutions and one or more deletions.

In one embodiment one amino acid residue is deleted. In another embodiment two amino acid residues are deleted.

In one embodiment of the invention one of the amino acid residues in the position B22-B30 or B25-B30 has been deleted and two have been substituted with another amino acid residue which may be the same or different.

In another embodiment of the invention one of the amino acid residues in the position B22-B30 or B25-B30 has been deleted and one has been substituted with another amino acid residue.

In a still further embodiment of the invention two of the amino acid residues in the position B22-B30 or B25-B30 have been deleted and one has been substituted with another amino acid residue.

In one embodiment the amino acid in position B30 is deleted.

In another embodiment the amino acid residue in position B29 is deleted.

In another embodiment the amino acid residue in position B28 is deleted.

In another embodiment the amino acid residue in position B27 is deleted.

In another embodiment the amino acid residue in position B26 is deleted.

In another embodiment the amino acid residue in position B25 is deleted.

In another embodiment the amino acid residues in position B26 and B30 have deleted.

In another embodiment the amino acid residues in position B25 and B30 have deleted.

In another embodiment the amino acid residues in position B27 and B30 have deleted.

In one embodiment the amino acid substitutions in position B22-B30 or B25-B30 are selected from Glu and/or Asp.

In a further embodiment the amino acid in position B22 is Glu.

In a further embodiment the amino acid in position B23 is Glu.

In a further embodiment the amino acid in position B24 is Glu.

In a further embodiment the amino acid in position B25 is Glu.

In a further embodiment the amino acid in position B26 is Glu.

In a further embodiment the amino acid in position B27 is Glu.

In a further embodiment the amino acid in position B28 is Glu.

In a further embodiment the amino acid in position B29 is Glu.

In a further embodiment the amino acid in position B22 is Asp.

In a further embodiment the amino acid in position B23 is Asp.

In a further embodiment the amino acid in position B24 is Asp.

In a further embodiment the amino acid in position B25 is Asp.

In a further embodiment the amino acid in position B26 is Asp.

In a further embodiment the amino acid in position B27 is Asp.

In a further embodiment the amino acid in position B28 is Asp

In a further embodiment the amino acid in position B29 is Asp.

Other suitable amino acid residues for substitution of the amino acid residues in position B22-B30 or B25-B30 are His and Pro. Also the B30 amino acid residue may be substituted with Lys.

In one embodiment the amino acids in position B26 and position 30 have been deleted and the amino acid residue in position B28 has been substituted with another amino acid residue.

In another embodiment the amino acids in position B26 and position 30 have been deleted and the amino acid residue in position B27 has been substituted with another amino acid residue.

In another embodiment the amino acids in position B25 and position 30 have been deleted and the amino acid residue in position B28 has been substituted with another amino acid residue.

In another embodiment the amino acids in position B25 and position 30 have been deleted and the amino acid residue in position B27 has been substituted with another amino acid residue.

In another aspect the present invention is related to use of the insulin analogues according to the invention for the treatment of diabetes.

In a further aspect the present invention is related to a pharmaceutical formulation comprising the fast acting insulin analogues of the invention and optionally one or more agents suitable for stabilization, preservation or isotonicity, for example, zinc ions, phenol, cresol, a parabene, sodium chloride, glycerol or mannitol. The zinc content of the formulations may be between 0 and about 4 zinc atoms per insulin hexamer.

Thus, in one embodiment the present invention is related to a pharmaceutical formulation comprising a fast acting insulin analogues in which at least one of the natural amino acid residues in position B22-B30 or B25-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 or B25-B30 optionally have been deleted together with suitable adjuvants and additives such as one or more agents suitable for stabilization, preservation or isotoni, for example, zinc ions, phenol, cresol, a parabene, sodium chloride, glycerol or mannitol.

The invention also provides soluble compositions that are mixtures of a fast acting insulin analogues according to the present invention and long acting insulin analogues or derivative wherein the rate of in vivo disappearance of the fast acting insulin analogue and the long acting insulin analogue or derivative respectively from the site of injection is the same or substantially the same as when injected in separate compositions.

Thus in another aspect the present invention is related to a soluble pharmaceutical formulation comprising a fast acting human insulin analogue according to the present invention in mixture with a long acting human insulin analogue or derivative together with suitable adjuvants and additives such as one or more agents suitable for stabilization, preservation or isotoni, for example, zinc ions, phenol, cresol, a parabene, sodium chloride, glycerol or mannitol.

The zinc content may be between 0 and about 4 zinc atoms per insulin hexamer. The pH of the pharmaceutical preparation may be between about 3 and about 8.5, between about 3 and about 5 or between about 6.5 and about 7.5.

In one embodiment the invention is related to a pharmaceutical formulation comprising a fast acting insulin analogue in which at least one of the natural amino acid residues in position B22-B30 or B25-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 or B25-B30 optionally have been deleted in mixture with a long acting human insulin analogue or derivative together with suitable adjuvants and additives such as one or more agents suitable for stabilization, preservation or isotoni, for example, zinc ions, phenol, cresol, a parabene, sodium chloride, glycerol or mannitol.

In one embodiment of the invention the long acting human insulin derivative is an acylated derivative of human insulin. Acylated insulin derivatives may be such wherein a lipophilic group is attached to the lysine residue in position B29 or B1. Illustrative representatives of acylated insulins are disclosed in EP patent No. 792290. A commercial product is Levemir® comprising Lys$^{B29}$(N$^{\epsilon}$-tetradecanoyl) des(B30) human insulin (insulin detemir) as the active component.

Thus, in a further embodiment the invention is related to a pharmaceutical formulation comprising a fast acting insulin analogue in which at least one of the natural amino acid residues in position B22-B30 or B25-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 optionally have been deleted in mixture with a long acting acylated human insulin derivatives together with suitable adjuvants and additives such as one or more agents suitable for stabilization, preservation or isotoni, for example, zinc ions, phenol, cresol, a parabene, sodium chloride, glycerol or mannitol.

Other examples of long acting insulins are such comprising positively charged amino acids such as Arg attached to the C-terminal end of the B-chain as disclosed in U.S. Pat. No. 5,656,722. A commercial product is Lantus® comprising A21Gly, B31Arg, B32Arg human insulin (insulin glargine).

Thus, in a further embodiment the invention is related to a pharmaceutical formulation comprising a fast acting insulin analogue in which at least one of the natural amino acid residues in position B22-B30 or B25-B30 in the human B-chain has been substituted with another amino acid residue having the effect of promoting formation of the monomeric form of insulin, the His amino acid residue in position 10 in the B-chain is substituted with a Gln and wherein further one or more of the amino acid residues in position B22-B30 or B25-B30 optionally have been deleted in mixture with a long acting insulin analogue having at one or two additional positive charges compared to human insulin together with suitable adjuvants and additives such as one or more agents suitable for stabilization, preservation or isotoni, for example, zinc ions, phenol, cresol, a parabene, sodium chloride, glycerol or mannitol.

In one embodiment the invention is relates to a pharmaceutical composition comprising a fast acting insulin analogue according to the invention in mixture with Lys$^{B29}$(N$^{\epsilon}$-tetradecanoyl) des(B30) human insulin (insulin detemir).

In another embodiment the invention is relates to a pharmaceutical composition comprising a fast acting insulin analogue according to the invention in mixture with Lys$^{B29}$(N$^{\epsilon}$-(N-lithocholyl-γ-glutamyl)) des(B30) human insulin.

In a further embodiment the invention is relates to a pharmaceutical composition comprising a fast acting insulin analogue according to the invention in mixture with N$^{\epsilon B29}$-(N$^\alpha$-(HOOC(CH$_2$)$_{14}$CO)-γ-Glu) des(B30) human insulin.

In a further embodiment the invention is relates to a pharmaceutical composition comprising a fast acting insulin analogue according to the invention in mixture with A21Gly, B31Arg, B32Arg human insulin (insulin glargine).

In a further aspect the present invention is related to the use of the fast acting insulin analogues according to the present invention for the preparation of a pharmaceutical preparation for the reducing of blood glucose level in mammalians in particularly for the treatment of diabetes optionally in mixture with a long acting human insulin analogue or derivative.

In a further embodiment the present invention is related to a method of reducing the blood glucose level in mammalians by administrating a therapeutically active dose of a fast acting insulin analogue according to the invention to a patient in need of such treatment optionally in mixture with a long acting human insulin analogue or derivative.

Figure 1:
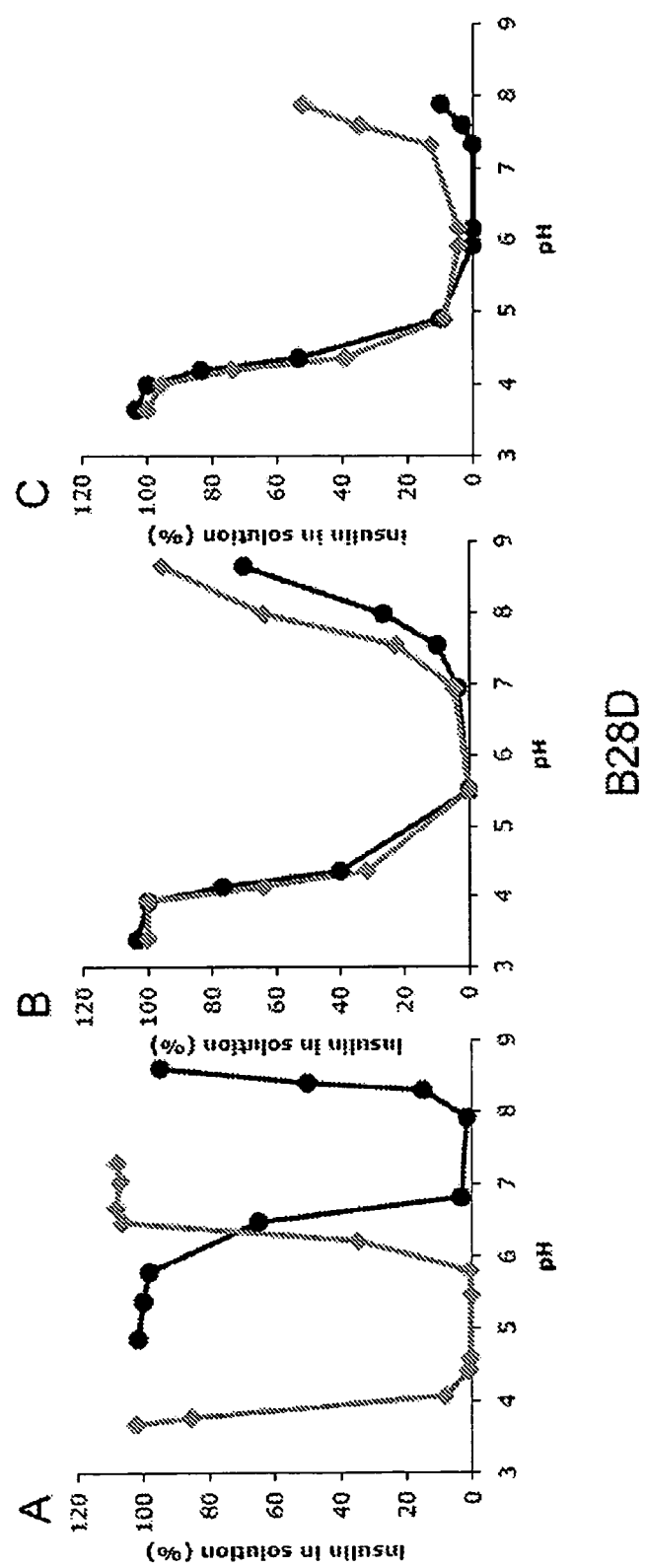
FIG. 1 shows the equilibrium solubility of insulin aspart (B28Asp human insulin) and of insulin glargine (A21Lys, B31Arg, B32Arg human insulin). Panel A: solubility in individual preparations in pure water. Panel B: solubility in a mixed preparation of 0.3 mM insulin aspart and 0.3 mM insulin glargine comprising 0.3 mM Zn$^{2+}$, 16 mM m-cresol, 16 mM phenol and 1.6% glycerol. Panel C: solubility in a mixed preparation of 0.3 mM insulin aspart with 0.3 mM insulin glargine comprising 120 mM NaCl, 1.6% glycerol. In each panel the solubility of insulin aspart is represented by grey markers and the solubility of insulin glargine is represented by black markers, the lines connecting the individual measuring points are meant as guidance for the eye.
Figure 2:
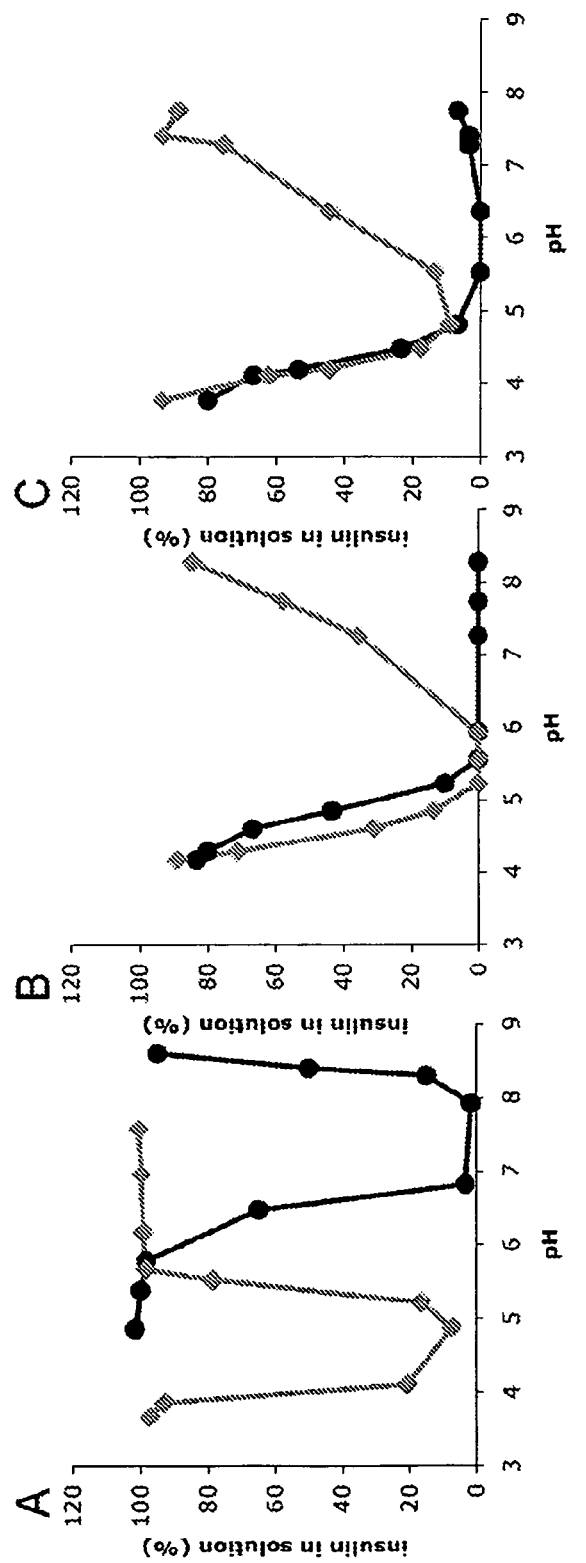
FIG. 2 shows the equilibrium solubility of B10Q, desB26, B28E, desB30 human insulin and of insulin glargine. Panel A: solubility in individual preparations in pure water. Panel B: solubility in a mixed preparation of 0.3 mM B10Q, desB26, B28E, desB30 insulin and 0.3 mM insulin glargine comprising 0.3 mM Zn$^{2+}$, 16 mM m-cresol, 16 mM phenol and 1.6% glycerol. Panel C: solubility in a mixed preparation of 0.3 mM B10Q, desB26, B28E, desB30 insulin and 0.3 mM insulin glargine comprising 120 mM NaCl, 1.6% glycerol. In each panel the solubility of B10Q, desB26, B28E, desB30 insulin is represented by grey markers and the solubility of insulin glargine is represented by black markers, the lines connecting the individual measuring points are meant as guidance for the eye.
Figure 3:
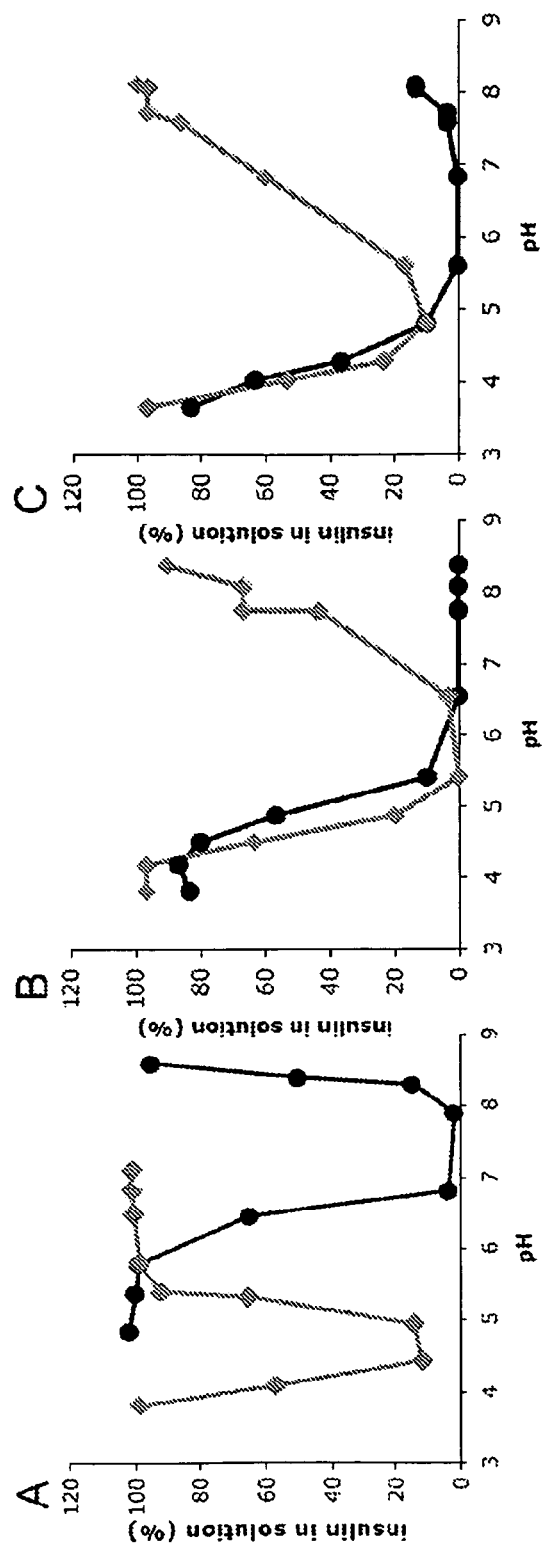
FIG. 3 shows the equilibrium solubility of B10Q, desB25, B28E, desB30 insulin and of insulin glargine. Panel A: solubility in individual preparations in pure water. Panel B: solubility in a mixed preparation of 0.3 mM B10Q, desB25, B28E, desB30 insulin and 0.3 mM insulin glargine comprising 0.3 mM Zn$^{2+}$, 16 mM m-cresol, 16 mM phenol and 1.6% glycerol. Panel C: solubility in a mixed preparation of 0.3 mM B10Q, desB25, B28E, desB30 insulin and 0.3 mM insulin glargine comprising 120 mM NaCl, 1.6% glycerol. In each panel the solubility of B10Q, desB25, B28E, desB30 insulin is represented by grey markers and the solubility of insulin glargine is represented by black markers, the lines connecting the individual measuring points are meant as guidance for the eye.
Figure 4:
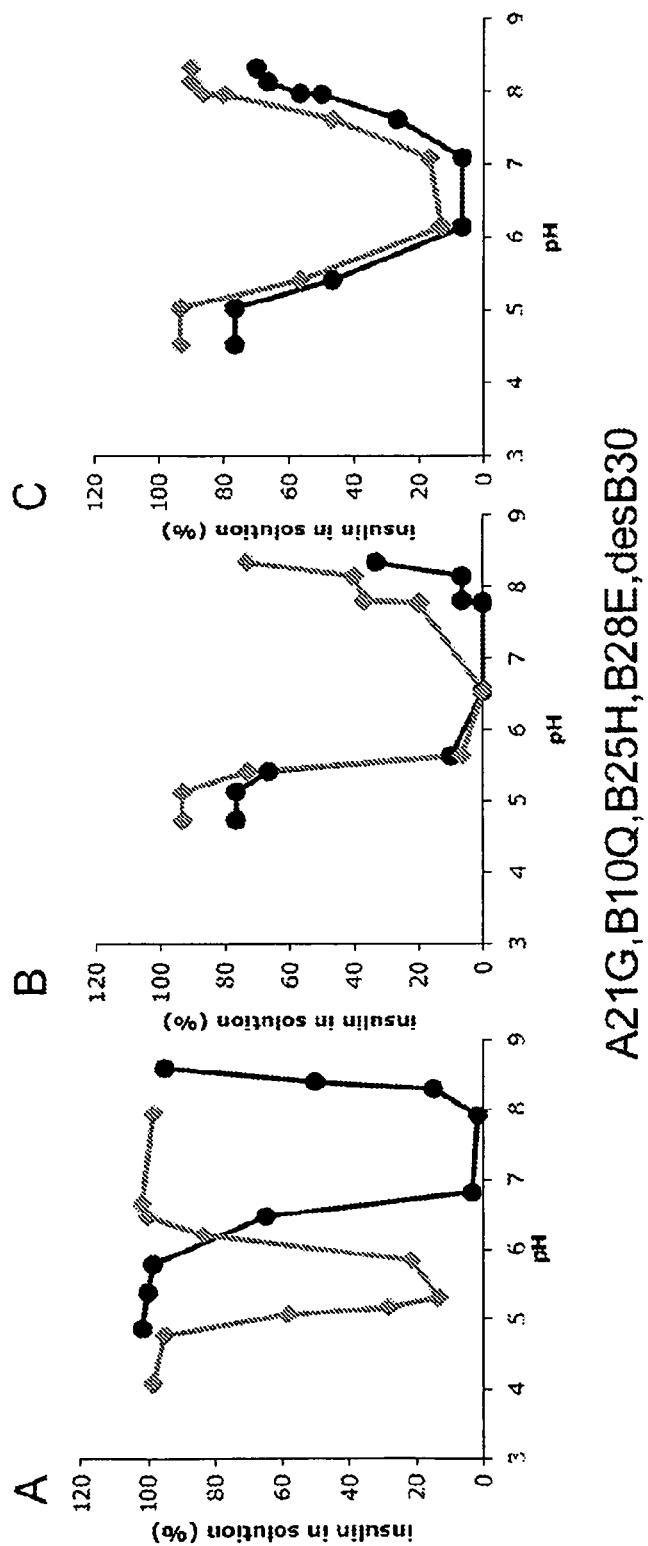
FIG. 4 shows the equilibrium solubility of A21G, B10Q, B25H, B28E, desB30 insulin and of insulin glargine. Panel A: solubility in individual preparations in pure water. Panel B: solubility in a mixed preparation of 0.3 mM A21G, B10Q, B25H, B28E, desB30 insulin and 0.3 mM insulin glargine comprising 0.3 mM Zn$^{2+}$, 16 mM m-cresol, 16 mM phenol and 1.6% glycerol. Panel C: solubility in a mixed preparation of 0.3 mM A21G, B10Q, B25H, B28E, desB30 insulin and 0.3 mM insulin glargine comprising 120 mM NaCl, 1.6% glycerol. In each panel the solubility of A21G, B10Q, B25H, B28E, desB30 insulin is represented by grey markers and the solubility of insulin glargine is represented by black markers, the lines connecting the individual measuring points are meant as guidance for the eye.

a) is a preparation comprising 0.6 mM B10Q, desB26, B28E, desB30 human insulin, 19 mM phenol, 19 mM m-cresol and 1.6% glycerol, pH 3.23 b) is a 3:7 mixture of a) and Lantus®, pH=3.74 c) is a mixture comprising 0.18 mM B10Q, desB26, B28E, desB30 human insulin and 1.68 mM insulin detemir and 0.84 mM Zn, 19 mM phenol, 19 mM m-cresol, 1.6% glycerol and 10 mM NaCl, pH 7.39, and

DESCRIPTION OF THE INVENTION

The insulins according to the present invention are modified at certain positions in the insulin molecule which have an impact on the formation of dimers and hexamers and the insulin analogues according to the present invention are characterized by the possibility of forming soluble mixed formulations (pre-mixed or self-mixed) with long acting insulin analogues. Fast action is achieved through monomerizing substitutions/deletions in the B chain C-terminus and mixability with long acting insulin analogues is achieved through a substitution of the Zn-binding His in position B10.

Substitutions of one or more of the amino acid residues in the C-terminal end of the B-chain of human insulin to obtain a monomeric and thus a fast acting insulin analogue are well known from e.g. EP 214826.

Both the B-chain and the A-chain may comprise additional mutations further to the mutations according to the invention as long as the resulting insulin molecule still has the desired properties, that is being fast acting, soluble and mixable with long acting insulin analogues or derivatives to form a soluble mixture without blunting. Such further mutations may have a stabilizing effect on either the physical or the chemical stability or both of the modified insulin molecule.

In one embodiment the insulin analogues according to the present invention are selected from the group consisting of: B10Q, B28E, desB30 human insulin; B10Q, B27E, desB30 human insulin; B10Q, B26E, desB30 human insulin; and B10Q, B25E, desB30 human insulin.

In another embodiment the insulin analogues according to the present invention are selected from the group consisting of B10Q, B28E, desB30, A21G human insulin; 10Q, B27E, desB30, A21 G human insulin; B10Q, B26E, desB30, A21G human insulin; and B10Q, B25E, desB30, A21G human insulin.

In another embodiment the insulin analogues according to the present invention are selected from the group consisting of B10Q, des B27, B28E, desB30 human insulin; B10Q, des B26, B28E, desB30 human insulin; and B10Q, des B25, B28E, desB30 human insulin.

In another embodiment the insulin analogues according to the present invention are selected from the group consisting of B10Q, des B27, B28E, desB30, A21G human insulin; B10Q, des B26, B28E, desB30, A21G human insulin; and B10Q, des B25, B28E, desB30, A21G human insulin.

In another embodiment the insulin analogues according to the present invention are selected from the group consisting of B10Q, B28E human insulin; B10Q, B27E human insulin; B10Q, B26E human insulin; and B10Q, B25E human insulin.

In another embodiment the insulin analogues according to the present invention are selected from the group consisting of B10Q, B28E A21G human insulin; 10Q, B27E, A21G human insulin; B10Q, B26E, A21G human insulin; and B10Q, B25E, A21G human insulin.

In another embodiment the insulin analogues according to the present invention are selected from the group consisting of B10Q, des B27, B28E human insulin; B10Q, des B26, B28E human insulin; and B10Q, des B25, B28E human insulin.

In another embodiment the insulin analogues according to the present invention are selected from the group consisting of B10Q, des B27, B28E, A21G human insulin; B10Q, des B26, B28E, A21G human insulin; and B10Q, desB25, B28E, A21G human insulin.

The fast acting insulin analogues according to the invention can be mixed with long acting insulin analogues or derivatives without a blunting effect. With blunting is meant that the activity profile of the fast acting and long acting insulin respectively are changed in the mixture so that the fast acting insulin becomes slower and the long acting insulin becomes faster.

Thus the term "no blunting" as used herein means that when formulated in one formulation both the fast acting insulin and the long acting insulin have a profile of action which is identical or substantially identical to the profile of action when administered in separate formulations.

The expression "substantial identical" will mean that the profile of action is at least 70-95% identical to the profile of action of the individual insulins when administered in separate formulations.

In one embodiment the profile of action of the individual insulins is at least 75% identical to the profile of action when administered in separate formulations.

In another embodiment the profile of action of the individual insulins is at least 85% identical to the profile of action when administered in separate formulations.

In another embodiment the profile of action of the individual insulins is at least 95% identical to the profile of action when administered in separate formulations.

The term "mixable" is used to characterize mixtures of the fast acting and long acting insulin where no or substantial no blunting occurs.

With a "fast acting" insulin is meant an insulin having a faster onset of action than normal or regular human insulin and with a "long acting insulin" is meant an insulin having a longer duration of action than normal or regular human insulin.

One group of long acting insulins are acylated insulin derivates. Human insulin has three primary amino groups: the N-terminal group of the A-chain and of the B-chain and the $\epsilon$-amino group of the lysine residue in position B29. Soluble insulin derivatives containing lipophilic substituents linked to the s-amino group of a lysine residue position B29 are disclosed in e.g. WO 95/07931 and WO 2005/1234.

The acyl group will be a liphophilic group and will typically be a fatty acid moiety comprising from about 6 to about 32, more typically from 6 to 24, from 8 to 20, from 12 to 20, from 12-16, from 10-16, from 10-20, from 14-18 or from 14-16 carbon atoms. Examples of fatty acids are capric acid, lauric acid, tetradecanoic acid (myristic acid), pentadecanoic acid, palmitic acid, heptadecanoic acid, stearic acid, dodecanoic acid, tridecanoic acid, and tetradecanoic acid. The acyl group may also be derived from a dicarboxylic fatty acid or it may be a lithocholic acid.

The acyl group may be attached directly to the free amino group in question. However, the acyl group may also be attached via amide bonds by a linker which links the free amino group in the insulin molecule and the acyl group in question together.

The acylated insulin may have one or two additional negative net charge compared to human insulin. The additional negative charge may be provided by a free carboxylic acid group in the fatty acid or by the linker group which may comprise one or more amino acid residues of which at least one will contain a free carboxylic acid or a group which is negatively charged at neutral pH.

Non limiting examples of acylated insulin analogues are $Lys^{B29}(N^\epsilon$-tetradecanoyl) des(B30) human insulin, $Lys^{B29}$ ($N^\epsilon$-hexadecanoyl) des(B30) human insulin; $Lys^{B29}(N^\epsilon$-tetradecanoyl) human insulin; $Lys^{B29}(N^\epsilon$-hexadecanoyl) human insulin; $Lys^{B29}(N^\epsilon$-(N-hexadecanoyl-$\gamma$-Glu) des(B30) human insulin; $Lys^{B29}(N^\epsilon$-(N-lithocholyl-$\gamma$-Glu)) des(B30) human insulin; $Lys^{B29}(N^\epsilon$-($\omega$-carboxyheptadecanoyl)) des (B30) human insulin; $Lys^{B29}(N^\epsilon$-($\omega$-carboxyheptadecanoyl)) human insulin, $N^{\epsilon B29}$-($N^\alpha$-(HOOC(CH$_2$)$_{13}$CO)-$\gamma$-Glu) des (B30) human insulin; $N^{\epsilon B29}$-($N^\alpha$-(HOOC(CH$_2$)$_{14}$CO)-$\gamma$-Glu) des(B30) human insulin; $N^{\epsilon B29}$-($N^\alpha$-(HOOC (CH$_2$)$_{15}$CO)-$\gamma$-Glu) des(B30) human insulin; $N^{\epsilon B29}$-($N^\alpha$-(HOOC(CH$_2$)$_{16}$CO) -$\gamma$-Glu) des(B30) human insulin; $N^{\epsilon B29}$-($N^\alpha$-(HOOC(CH$_2$)$_{17}$CO)-$\gamma$-Glu) des(B30) human insulin; $N^{\epsilon B29}$-($N^\alpha$-(HOOC(CH$_2$)$_{18}$CO)-$\gamma$-Glu) des(B30) human insulin; ($N^{\epsilon B29}$-($N^\alpha$-(HOOC(CH$_2$)$_{13}$CO) -$\gamma$-Asp) des(B30) human insulin; and $N^{\epsilon B29}$-($N^\alpha$-(HOOC(CH$_2$)$_{14}$CO)-$\gamma$-Asp) des(B30) human insulin.

A further type of long acting insulin analogues are disclosed in EP 368,187 which discloses insulin analogues having charged groups e.g. Arg attached to the C-terminal group B30, such as insulin glargine.

The mixability of the two components has been demonstrated by mixtures of fast acting insulin analogues according to the present invention with a long acting acylated insulin $Lys^{B29}(N^\epsilon$-tetradecanoyl) des(B30) human insulin (insulin detemir) and the long acting insulin analogue insulin glargine.

The fast acting insulins are produced by expressing a DNA sequence encoding a single-chain insulin precursor of the fast acting insulin in a suitable host cell by well known technique as disclosed in e.g. EP1,246,845. The insulin precursor is expressed in a transformed host cell as a precursor molecule which is converted into the desired insulin molecule by enzymatic and chemical in vitro processes as disclosed in EP 163,529 and EP 214,826. The precursor molecule may be expressed with an N-terminal extension which is later cleaved of as disclosed in EP 1246,845. Examples of N-terminal extensions of the type suitable in the present invention are disclosed in U.S. Pat. No. 5,395,922 and EP patent No. 765, 395.

The insulin precursor product for preparing the long acting, acylated insulin to be mixed with the fast acting insulin according to the invention can be produced by a method analogues to the methods described above. The insulin precursor can be acylated in the desired position as described e.g. in the EP 214,826, EP 375,437 and EP 383,472.

With "Insulin" as used herein is meant human insulin having the two chain structure of human insulin with disulfide bridges between $Cys^{A7}$ and $Cys^{B7}$ and between $Cys^{A20}$ and $Cys^{B19}$ and an internal disulfide bridge between $Cys^{A6}$ and $Cys^{A11}$, porcine insulin and bovine insulin.

The B-chain refers to the human insulin B-chain with 30 amino acid residues and the A-chain refers to the human insulin A-chain with 21 amino acid residues. Both the B-chain and the A-chain in the insulin analogues according to the present invention may comprise additional mutations further to the mutations according to the invention as long as the resulting insulin molecule still has the desired properties.

The number of further mutations will typically not be higher that 3 and will more typically be two or one.

Thus the amino acid residue in B1 may be substituted with another amino acid residue such as Asp or Gly or is deleted. Also Asn at position B3 may be mutated with Thr, Lys, Gln, Glu or Asp. The B-chain may also comprise an N-terminal extension and B1 may be deleted.

In the A chain Asn at position A21 may be mutated with Ala, Gln, Glu, Gly, His, Ile, Leu, Met, Ser, Thr, Trp, Tyr or Val, in particular with Gly, Ala, Ser, or Thr and preferably with Gly. Also A18 may be mutated with a Gln. Finally the A-chain may comprise a C-terminal extension such as A22 and A.23. The amino acid residue in position A22 and A22 may be a lysine residue which will give a good solubility in the acid pH range and further stabilizes the molecule against deamidation.

With "desB30 or B(1-29)" is meant a natural insulin B chain or an analogue thereof lacking the B30 amino acid residue and "A(1-21)" means the natural insulin A chain or an analogue or derivative thereof.

With an "insulin analogue" is meant a molecule with deviates from the natural molecule by one or more amino acid substitutions, additions or deletions and any combination thereof.

With an "insulin derivative" is meant an insulin molecule having a chemical group attached to one or more of the backbone amino acid residues.

The numbering of the positions in analogues according to the invention is based on the human insulin molecule. Thus with "B27" is meant the amino acid residue in position 27 in the B chain of human insulin (counted from the N-terminal end) and with "A1" is meant the amino acid residue in position 1 in the A chain of human insulin (counted from the N-terminal end), respectively. This numbering system is kept even if one or more of the natural amino acid residues have been deleted. Thus the insulin analogue named "B10Q, desB25, B28E, des B30 human insulin" will have the C-terminal sequence Thr-Asp-Lys in the B-chain.

The amino acid residues are indicated in the three letter amino acid code or the one letter amino code. Unless indicated explicitly, the amino acids mentioned herein are L-amino acids. Further, the left and right ends of an amino acid sequence of a peptide are, respectively, the N- and C-termini unless otherwise specified.

The term "monomeric insulin", when used herein, refers to human insulin analogs that are less prone to self-association (into dimers and hexamers) than human insulin.

Pharmaceutical Compositions

Compositions containing fast acting insulins of this invention optionally in mixture with a long acting insulin analogue or derivative can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin analogue or derivative employed, the age, body weight, physical activity, and diet of the patient, on a possible combination with other drugs, and on the severity of the state to be treated. It is recommended that the daily dosage of the insulin analogue or the mixtures of this invention be determined for each individual patient by those skilled in the art in a similar way as for known insulin compositions.

Usually, the pharmaceutical composition of this invention is administered subcutaneously. However the composition may also be used in insulin pumps and may be formulated for pulmunal administration.

The pharmaceutical composition will contain usual adjuvants and additives and are preferably formulated as an aqueous solution. The aqueous medium is made isotonic, for example, with sodium chloride, sodium acetate or glycerol. Furthermore, the aqueous medium may contain zinc ions, buffers and preservatives. The pH value of the composition is adjusted to the desired value and may be between about 3 to about 8.5, preferably between about 3 and about 5 or about 6.5 and about 7.5 depending on the isoelectric point, pI, of the insulin in question.

The fast acting insulin analogue and the long acting insulin can be mixed in a ratio of from about 10/90% about 30/70%, or about 50/50%. In one embodiment the molar ratio between the long acting and the fast acting insulin is greater than 2/1.

The buffer used in the pharmaceutical preparation according to the present invention may be selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

Pharmaceutically acceptable preservative are well known in the art. For convenience reference is made to Remington: The Science and Practice of Pharmacy, 19th edition, 1995.

The isotonicity agent may be selected from the group consisting of a salt (e.g. sodium chloride), a sugar or sugar alcohol, an amino acid or an alditol (e.g. glycerol (glycerine). The use of an isotonic agent in pharmaceutical compositions is well-known to the skilled person. For convenience reference is made to Remington: The Science and Practice of Pharmacy, 19th edition, 1995. The isotonic agent is typically present in a concentration from 1 mg/ml to 50 mg/ml. In a further embodiment the isotonic agent is present in a concentration from 1 mg/ml to 7 mg/ml, from 8 mg/ml to 24 mg/m or from 25 mg/ml to 50 mg/ml.

The present invention is described in further detail in the following examples which are not in any way intended to limit the scope of the invention as claimed. The attached Figures are meant to be considered as integral parts of the specification and description of the invention. All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

EXAMPLES

General Procedures

All expressions plasmids are of the C-POT type, similar to those described in EP 171, 142, which are characterized by containing the Schizosaccharomyces pombe triose phosphate isomerase gene (POT) for the purpose of plasmid selection and stabilization in S. cerevisiae. The plasmids also contain the S. cerevisiae triose phosphate isomerase promoter and terminator. These sequences are similar to the corresponding sequences in plasmid pKFN1003 (described in WO 90/100075) as are all sequences except the sequence of the EcoRI-XbaI fragment encoding the fusion protein of the leader and the insulin product. In order to express different fusion proteins, the EcoRI-XbaI fragment of pKFN1003 is simply replaced by an EcoRI-XbaI fragment encoding the leader-insulin fusion of interest. Such EcoRI-XbaI fragments may be synthesized using synthetic oligonucleotides and PCR according to standard techniques.

Yeast transformants were prepared by transformation of the host strain S. cerevisiae strain MT663 (MATalMATα pep4-3/pep4-3 HIS4/his4 tpk:LEU2/tpi::LEU2 Cir$^+$). The yeast strain MT663 was deposited in the Deutsche Sammlung von Mikroorganismen and Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM Na$_2$EDTA pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM Na$_2$EDTA, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM CaCl$_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM CaCl$_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium.

S. cerevisiae strain MT663 transformed with expression plasmids is grown in YPD for 72 h at 30° C. The expressed and secreted insulin precursor is isolated by conventional means and converted into the desired insulin analogue according to the invention by conventional in vitro enzymatic conversion as described above.

Example 1

Equilibrium Solubility of Insulin Formulations

Stock solutions of a fast acting insulin analogue or of a mixture of a fast acting insulin analogue and a long acting insulin (insulin glargine) containing either Zn$^{2+}$, phenol and glycerol concentrations close to marketed products or 120 mM NaCl were prepared and the pH was adjusted to the desired value corresponding to the alkaline endpoint of the pH-solubility profile. From these stock solutions samples were withdrawn, the pH adjusted to the desired value in the pH 3-8 range, and 0.3 ml samples were incubated at 23° C. for at least 4 days. After centrifugation (20,000 g for 20 minutes at 23 C) of each sample, pH was measured and the solubility was determined by quantification of insulin contents in the supernatant by Reverse Phase HPLC analysis on a XTerra RP8 Guard column (Waters), 50×20 mm, 5 micron particle size, eluted at 2 mL/minute at 35° C. or on a Gemini 3u C18 110A column (Phenomenex), 50×2.0 mm, 3 micron particle size eluted at 0.8 mL/minute at 35° C. Insulin is eluted with a phosphate buffer, pH=7.2, starting from approximately 7% (w/w) acetonitrile followed by a gradient step with increased acetonitrile to a concentration of approximately 65% (w/w).

The equilibrium solubility vs pH of several insulin analogues of the present invention (insulin aspart shown as a reference) in pure water or in mixed formulations with insulin glargine are shown in FIGS. 1-4. In each figure panel A represents the solubility in non-mixed formulations in water vs. pH of each insulin analogue compared to that of insulin glargine. Panel B and C are solubilities of each insulin in mixed formulations either in a preparation close to pharmaceutical formulation (panel B: 0.3 mM insulin analogue mixed with 0.3 mM insulin glargine and 0.3 mM Zn$^{2+}$, 16 mM m-cresol, 16 mM phenol and 1.6% glycerol) or in 120 mM NaCl, 1.6% glycerol (panel C: 0.3 mM insulin analogue and 0.3 mM insulin glargine comprising 1.6% glycerol, 120 mM NaCl), 120 mM NaCl compares to the ionic strength present in subcutis.

In Table 1 these solubilities are listed as "+" in the column with the heading "Lantus® mixability" when the solubility of the individual insulin analogue at neutral pH when mixed is not compromised compared to the solubility in separate preparations. In other terms when insulin glargine precipitates at neutral pH while the insulin analogue of the present invention is fully soluble, we expect the two analogues to be mixable and this is marked by "+" in Table 1.

Example 2

Glucose Utilization of Preparations of B10Q, desB26, B28E, desB30 Human Insulin and Insulin Glargine The glucose utilization effect following a subcutaneous injection of the insulin preparations of the present invention were characterized using a pig clamp model as described in Kurtzhals & Ribel, Diabetes 44, 1381-1385, (1995).

Figure 5:
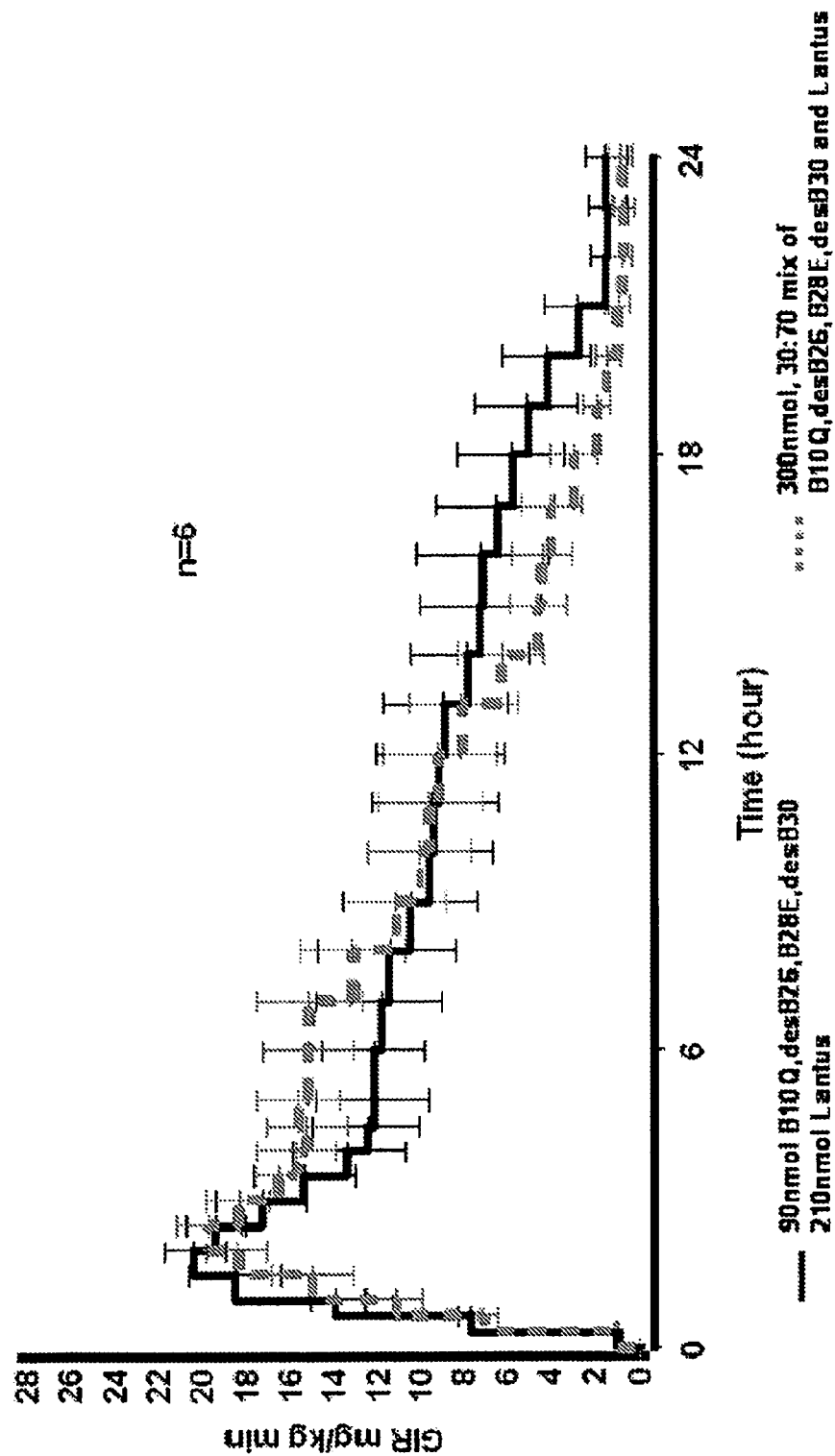
FIG. 5 shows a comparison of the glucose utilization in pigs following subcutaneous injection with either separate injections of 0.6 mM B10Q, desB26, B28E, desB30, 19 mM phenol, 19 mM m-cresol, 1.6% glycerol, pH=3.2 (a total of 90 nmol of the insulin analogue) and Lantus® (insulin glargine) (a total of 210 nmol insulin glargine), data shown in black, or with a single injection of a premixed 30:70 (molar basis) preparation of the two above mentioned insulins (a total of 300 nmol of the two insulin analogues), data shown in grey. The glucose infusion rate (GIR) is expressed as means±SE.

FIG. 5 compares glucose utilization in pigs following subcutaneous injection with either separate injections of 0.6 mM B10Q, desB26, B28E, desB30, 19 mM phenol, 19 mM m-cresol, 1.6% glycerol, pH=3.2 (a total of 90 nmol of the insulin analogue) and insulin glargine (a total of 210 nmol insulin glargine) or with a single injection of a premixed 30:70 (molar basis) preparation of the two above mentioned insulins (a total of 300 nmol of the two insulin analogues). The glucose utilization following injection of a mixed preparation compared to that following separate injections are indistinguishable within the experimental uncertainty.

Example 3

Figure 6:
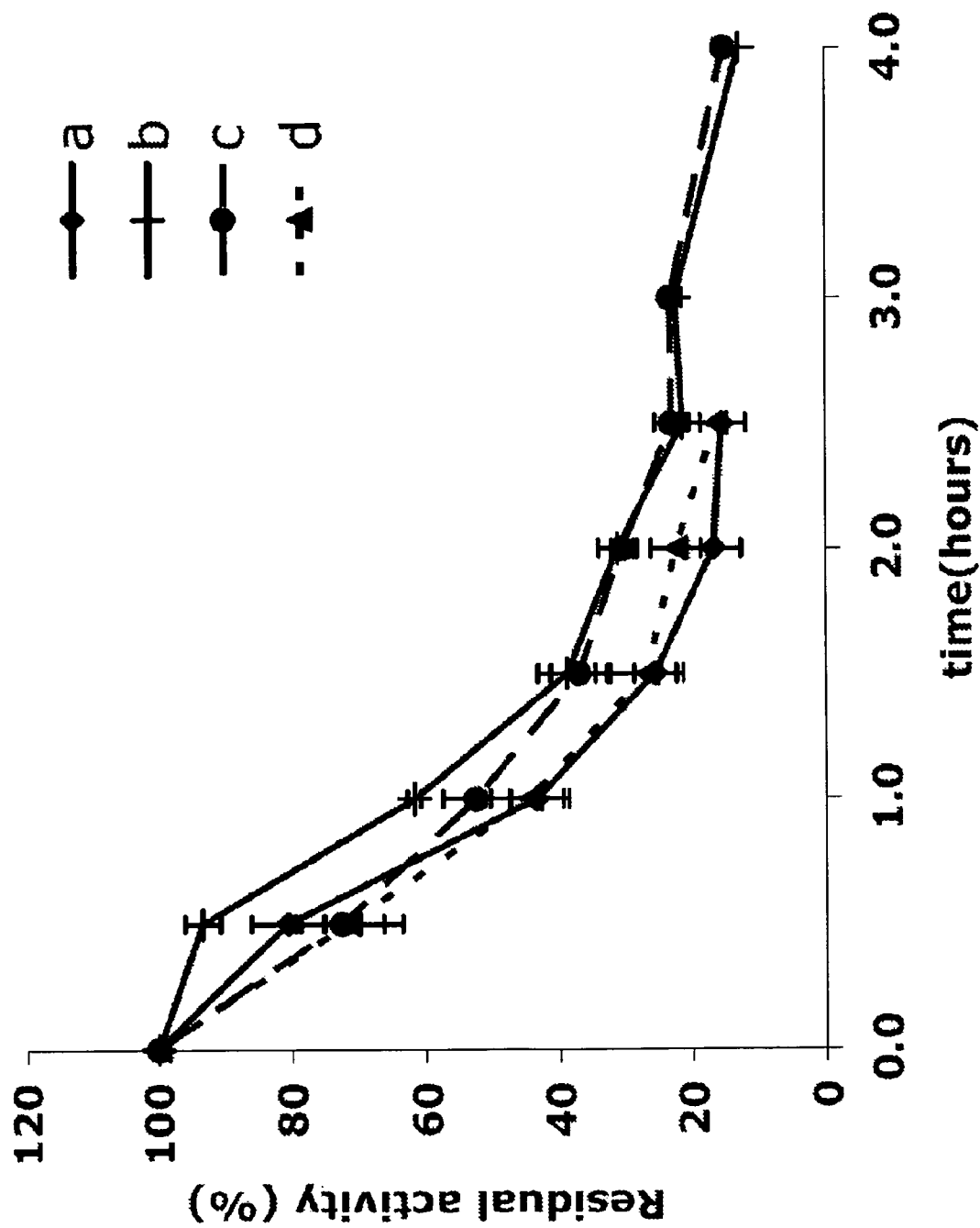
FIG. 6 shows the disappearance from the subcutaneous depot (pig model) of insulin preparations. Curves represent the disappearance of B10Q, desB26, B28E, desB30 human insulin in three different formulations a), b) and c) and the disappearance of insulin aspart in a NovoRapid® formulation d). The $T_{50\%}$ is as follows, a) 0.9±0.2, b) 1.3±0.2 and c) 1.1±0.3, d) 0.9±0.3.

The PK properties of a number of insulin analogues of the present invention in different formulations was characterized by the disappearance rate from the subcutaneous depot following subcutaneous injections in pigs. $T_{50\%}$ is the time when 50% of the A14 Tyr($^{125}$I) insulin has disappeared from the site of injection as measured with an external γ-counter (Ribel et al., The Pig as a Model for Subcutaneous Absorption in Man. In: M. Serrano-Rtios and P. J. Lefebre (Eds): Diabetes (1985) Proceedings of the 12$^{th}$ congress of the International Diabetes Federation, Madrid, Spain, 1985 (Excerpta Medica, Amsterdam (1986), 891-896). The $T_{50\%}$ values of a number of insulin analogues of the present invention is presented in table 1 and examples of disappearance curves are illustrated in FIG. 6. Serving as reference insulin aspart (B28D human insulin) in a NovoRapid® formulation has been included in all studies.

The test results are shown in Table 1 where

TABLE 1

| Substitutions | hIR binding (%) (1) | rFFC Potency (%) (2) | hIGF-1R binding (%) (3) | Disapp. $T_{50\%}$ (hours) (4) | Disapp $T_{50\%}$ (hours), mix with Levemir® (5) | Disapp $T_{50\%}$ (hours), mix with Lantus® (6) | Lantus® Mixability (7) | Insulin detemir mixability. Measured (theoretical) (8) | Monomer → 1 mM (NUV-CD) (9) |
|---|---|---|---|---|---|---|---|---|---|
| B28D | 88 | | 43 | | | | | 11:89 (36:64) | |
| A18Q, B10Q, B28E, desB30 | | | | | | | | 37:63 (36:64) | |
| B10Q, B28E, desB30 | 124 | 144 | 47 | | | | | | + |
| B10Q, desB27, B28E, desB30 | 115 | 141 | 26 | 0.8 ± 0.2; 0.6 ± 0.2; 0.8 ± 0.1 | 1.1 ± 0.2 (0.3:1.2 mM) | 1.1 ± 0.3 (0.3:0.3 mM); 1.3 ± 0.3 (0.18:0.42 mM) | + | | + |
| B10Q, B22E, B28E, desB30 | | 90 | 7 | | | | + | | + |
| B10Q, desB26, B28E, desB30 | 47 | 85 | 4 | 0.9 ± 0.2 | 1.1 ± 0.3 (0.18:1.68 mM) | 1.3 ± 0.2 (0.18:0.42 mM) | + | | + |
| B10Q, B26E, B28E, desB30 | 163 | | 10 | | | | | | + |
| B10Q, desB25, B28E, desB30 | 105 | 158 | 34 | | | | + | | + |
| B10Q, B25H, B28E, desB30 | 45 | | 7 | 0.8 ± 0.3; 0.7 ± 0.1 | 1.0 ± 0.2 (0.3:1.2 mM) | 2.1 ± 0.2 (0.3:0.3 mM) | + | 25:75 (25:75) | + |
| A21G, desB1, B3T, B10Q, B28D, B29P, B30K | 85 | 88 | 44 | | | | + | 25:75 (25:75) | + |
| A21G, B10Q, desB27, B28E, desB30 | 72 | | 39 | | | | | | + |
| A21G, B10Q, B25H, B28E, desB30 | 33 | 83 | | | | | + | 25:75 (25:75) | + |
| A21G, desB1, B3Q, B10Q, B28E, desB30 | 91 | | 48 | | | | + | | + |
| A21G, desB1, B3Q, B10Q, B25H, B28E, desB30 | 32 | 71 | | | | | + | | + |
| A22K, B3T, B10Q, desB27, B28E, desB30 | 96 | 59 | 76 | | | | + | | + |

(1) refers to Biochemical methods assay (II),
(2) refers to Biochemical methods assay (III),
(3) refers to Biochemical methods assay (IV),
(4) refers to formulations of 0.6 mM insulin analogue, 19 mM phenol, 19 mM m-cresol, 1.6% glycerol, pH between 3.0 and 4.0 measured as described in Example 3.
(5) refers to formulations of 0.18 mM insulin analogue, 1.68 mM insuliln detemir, 0.84 mM Zn, 19 mM phenol, 19 mM m-cresol, 1.6% glycerol, 10 mM NaCl pH~7.4 or 0.3 mM insulin analogue, 1.2 mM insulin detemir, 0.84 mM Zn, 19 mM phenol, 19 mM m-cresol, 1.6 % glycerol, 10 mM NaCl pH~7.4 measured as described in Example 3,
(6) refers to mixtures of formulation of (4) with Lantus ®, molar ratio as listed. Measured as described in Example 3,
(7) refers to solubility of individual insulin species, measured as described in Example 1.
(8) refers to mixability measured by size exclusion chromatography, biochemical methods assay (I). Reported are the measured distribution on material eluting as monomer and hexamer respectively and in parenthesis the theoretical distribution as calculated from the molar ratio. Insulin detemir in this system elutes as part monomer and part hexamer, and
(9) refers to NUV-CD method, biochemical methods assay (VI).

Pharmacological Methods

Assay (I)

Size exclusion chromatography (SEC) was performed essentially as described in Havelund et al. 2004 Pharmaceutical research, 21, 1498-1504. The chromatographic system was a Superose 6 HR PC 6/30 column (GE healthcare) eluted by tris-buffered isotonic saline (NaCl 140 mM, tris/HCl 10 mM, $NaN_3$ 0.01%, pH 7.5 at 37° C., injecting 1% of column volume and using a flow of 90 min per column volume and UV detection at 276 nm. The references were a stable insulin monomeric insulin X2 (AspB9, GluB27 human insulin, zinc free), a stable hexameric insulin: Co(III) insulin, albumin (HSA), and covalent albumin (formed in solution).

Assay (II)

Insulin Receptor Binding

The affinity of the insulin analogues for the human insulin receptor can be determined by a SPA assay (Scintillation Proximity Assay) microtiterplate antibody capture assay. SPA-PVT antibody-binding beads, anti-mouse reagent (Amersham Biosciences, Cat No. PRNQ0017) are mixed with 25 ml of binding buffer (100 mM HEPES pH 7.8; 100 mM sodium chloride, 10 mM $MgSO_4$, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[125I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl is then added and a dilution series is made from appropriate samples. To the dilution series is then added 100 µl of reagent mix and the samples are incubated for 16 hours while gently shaken. The phases are then separated by centrifugation for 1 min and the plates counted in a Topcounter. The binding data are fitted using the nonlinear regression algorithm in the GraphPad Prism 2.01 (GraphPad Software, San Diego, Calif.).

Assay (III)

Biological Potency of Insulin Analogues, Rat Free Fat Cell Assay

Rats are killed, and the epididymale fat pads removed and placed in degradation buffer. Degradation is carried out at 37° C. under vigorously shaking for 1 h. The cell suspension is filtrated in order to remove tissue debris, and the adipocytes are washed twice and resuspended in incubation buffer. 0.1 ml cell suspension is incubated at 37° C. under gentle shaking with 10 µl glucose solution and 10 µl insulin or other compound for two hours. The incubation is stopped by adding 150 µl scintillator and counted.

Calculation of the potency is done by comparing EC50 for an internal standard and the unknown sample. Fitting of curves is a four parameter logistic model expecting constant minimum and maximum response.

Assay (IV)

Binding of Insulin Analogues to the Human Insulin-Like Growth Factor-1 Receptor (hIGF-1R)

The affinity of insulin analogues for the human insulin-like growth factor-1 receptor (hIGF-1R) can be determined by a SPA (Scintillation Proximity Assay) microtiter plate antibody capture assay. Anti-Mouse PVT SPA beads (500 mg, GE Life Sciences # RPNQ0017) are mixed with 25 ml of binding buffer (100 mM HEPES, 100 mM NaCl, 10 mM MgSO4, 0.025% Tween-20, pH=7.8). Reagent mix for a single 96-well microtiter plate (Optiplate-96 Perkin-Elmer #6005190) is composed of 40 µl of purified recombinant hIGF-1R (Novo Nordisk A/S), 12 µl of a 1:16 dilution of monoclonal antibody against hIGF-1R (clone 24-31), 3 ml of SPA beads suspension and binding buffer to a total of 12 ml. To 25 µl of a dilution series of IGF-1, insulin or insulin analogue is then added 100 µl of reagent mix and 25 µl of a dilution of [125I]A14Tyr-human IGF-1 corresponding to 10,000 cpm. The samples are incubated for 16 hours at room temperature while gently agitated. The plate is then centrifugated for 1 min at 1,000 rpm prior to counting in a Packard TopCount NXT. The binding data are fitted using the four-parameter nonlinear regression algorithm (sigmoidal dose-response) in GraphPad Prism 4.03 (GraphPad Software, San Diego, Calif.).

Assay (V)

Mixability of Insulin Analogues with Long Acting Analogues, NMR Based Method.

Signals from proteins and peptides in NMR spectra are very sensitive to the local chemical environment. As a result we can use NMR signals to probe for mixability of insulins. For $^{15}N$ labelled desB30 insulin the positions of signals from NH groups in a $^1H$-$^{15}N$ HSQC NMR spectra are known. Changes in the $^1H$-$^{15}N$ NMR spectra when mixing $^{15}N$ labelled desB30 insulin with an unlabelled analogue can be monitored. $^1H$-$^{15}N$ HSQC NMR spectra of desB30 insulin and a NMR spectrum of desB30 mixed with an analogue are compared. If new peaks appear in the $^1H$-$^{15}N$ HSQC spectrum of $^{15}N$ desB30 when an analogue is present in the mixture it indicates changes in the local environment of a NH group in $^{15}N$ desB30 insulin. This again shows that mixed dimers/hexamers have been formed meaning that the two components are not mixable.

$^1H$-$^{15}N$ HSQC NMR spectra were recorded on a Varian (nova 600 NMR spectrometer equipped with a cold probe. All data were recorded at a temperature of 37 C. Insulins ($^{15}N$ desB30 and a selected analogue) were dissolved separately in water, mixed, and the final solvent system is: 30 mM phenol-d, 10 mM NaCl, 14 mg/ml propylenglycol-d and 8 mM phosphate buffer pH 7.4, 0.1 mM Zn, 90% $H_2O$/10% $D_2O$.

Insulin concentrations were 0.2 mM $^{15}N$ desB30 and 0.05 mM of the selected insulin analogue. For comparison a NMR spectrum of 15N desB30 was recorded under identical solvent conditions.

When testing the insulin analogues according to the present invention in this assay most of the analogues turned out to be mixable with the desB30 insulin indicating that they will also be mixable with insulin detemir having the same amino acid composition in this area of the molecule as desB30 insulin except for the added acyl group in B29.

Assay (VI)

Assessment of Monomer/Dimer Equilibrium, NUV-CD Based Method.

Monomerization of insulin analogues, NUV-CD

The NUV-CD (near UV circular dichroism) spectrum in the 350-250 nm range reflects the environment of the tyrosine chromophores and is very sensitive to aggregation and is therefore useful as a reporter of the equilibrium between monomer and dimer/higher aggregates, the numerical value begin low for monomeric species (low concentration) and higher for dimeric species (cf. human insulin at the highest concentrations).

NUV CD spectra were recorded at 20 C using a Jasco J-715 spectropolarimeter calibrated with (+)-10-camphorsulfonic acid. The CD is expressed as Δε (M-1 cm-1) normalized to the molar concentration of protein in the near-UV range (250-350 nm), and the signal at 276 nm vs. concentration is used as a reporter of monomerization.

In Table 1 a "+" in the column with the heading "Monomer—) 1 mM (NUV-CD)" indicates that the tested insulin analogue was predominantly in the monomeric form.

The invention claimed is:

1. A fast acting insulin analogue, the insulin analogue consisting of two polypeptide chains, a human A-chain and a human B-chain, the human B chain comprising a substitution, wherein an amino acid residue in position B28 in the human B-chain is substituted with a Glu residue, and wherein the natural His amino acid residue in position 10 in the B-chain is substituted with a Gln and optionally one or more of amino acid residues in position B22-B30 in the human B-chain have been deleted.

2. The fast acting insulin analogue according to claim 1, wherein an additional amino acid residue in position B22-B30 in the human B-chain is substituted with a Glu or an Asp residue.

3. The fast acting insulin analogue according to claim 1, wherein an additional amino acid residue in position B25-B30 in the human B-chain is substituted with a Glu or an Asp residue.

4. The fast acting insulin analogue according to claim 2 wherein the amino acid in position B27 is Glu.

5. The fast acting insulin analogue according to claim 1, wherein the amino acid in position B30 is deleted.

6. The fast acting insulin analogue according to claim 1, wherein the one or more of amino acid residues in position B22-B30 in the human B-chain have been deleted is selected from the group consisting of amino acid in positions B25, B26 and B27.

7. The fast acting insulin analogue according to claim 6 for the use of treatment of diabetes.

8. A pharmaceutical formulation comprising an insulin analogue according to claim 1 in mixture with a long acting insulin analogue or derivative.

9. A pharmaceutical formulation according to claim 8, wherein the long acting insulin is an acylated insulin derivative.

10. A pharmaceutical composition according to claim 9, wherein the long acting acylated insulin is $Lys^{B29}(N^{\epsilon}$-tetradecanoyl) des(B30) human insulin (insulin detemir).

11. A pharmaceutical composition according to claim 9, wherein the long acting insulin is A21Gly, B31Arg, B32Arg human insulin (insulin glargine).

* * * * *

UNITED STATES PATENT AND TRADEMARK OFFICE
CERTIFICATE OF CORRECTION

| | | |
|---|---|---|
| PATENT NO. | : 8,575,096 B2 | Page 1 of 1 |
| APPLICATION NO. | : 12/673226 | |
| DATED | : November 5, 2013 | |
| INVENTOR(S) | : Olsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this
Tenth Day of November, 2015

Michelle K. Lee
*Director of the United States Patent and Trademark Office*